United States Patent [19]

Hulshof

[11] Patent Number: 5,226,943
[45] Date of Patent: Jul. 13, 1993

[54] HERBICIDES AND FUNGICIDES CONTAINING ACTIVITY PROMOTING ADDITIVES

[75] Inventor: Willem T. Hulshof, Putten, Netherlands

[73] Assignee: Akzo N.V., Netherlands

[21] Appl. No.: 730,387

[22] Filed: Jul. 15, 1991

Related U.S. Application Data

[63] Continuation of Ser. No. 384,074, Jul. 24, 1989, abandoned, which is a continuation of Ser. No. 78,654, Jul. 28, 1987, abandoned.

[30] Foreign Application Priority Data

Aug. 20, 1986 [NL] Netherlands .......................... 8602115

[51] Int. Cl.$^5$ ............................................. A01N 33/04
[52] U.S. Cl. ............................... 504/116; 71/DIG. 1; 504/258
[58] Field of Search ...................... 71/86, 121, DIG. 1, 71/79

[56] References Cited

U.S. PATENT DOCUMENTS

| | | | |
|---|---|---|---|
| 3,110,732 | 11/1963 | Speranza et al. | 564/505 |
| 3,118,000 | 1/1964 | Dupré et al. | 564/505 |
| 3,121,750 | 2/1964 | De Groote et al. | 564/505 |
| 3,456,012 | 7/1969 | Swenson | 564/505 |
| 3,574,755 | 4/1971 | McConnell et al. | 564/505 |
| 4,075,002 | 2/1978 | Drewe et al. | 71/92 |
| 4,440,562 | 4/1984 | Prill | 71/86 |
| 4,528,023 | 7/1985 | Ahle | 71/86 |

FOREIGN PATENT DOCUMENTS

| | | |
|---|---|---|
| 0006348 | 1/1980 | European Pat. Off. . |
| 0070702 | 1/1983 | European Pat. Off. . |
| 0290416 | 4/1988 | European Pat. Off. . |
| 60-51102 | 3/1985 | Japan . |
| 60-75324 | 4/1985 | Japan . |
| 131437 | 10/1986 | Poland . |
| 998264 | 7/1965 | United Kingdom . |
| 2022416 | 12/1979 | United Kingdom . |

OTHER PUBLICATIONS

Wyrill et al "Glyphosate Toxicity to . . . as Influenced by Surfactants", vol. 25, Issue 3 Weed Science, 275-287, 1977.

*The Herbicide Glyphosate*, Ed. Grossbard et al, Butterworths & Co Ltd, 1985, p. 224.

Turner, "Effect of Ammonium Sulphate and Other Additives Upon the Phytotoxicity of Glyphosate to Agropyron Repens (L.) Beauv", Weed Research, 1980, vol. 20, 139-146.

*Primary Examiner*—Richard L. Raymond
*Assistant Examiner*—B. Bembenick
*Attorney, Agent, or Firm*—Oliff & Berridge

[57] ABSTRACT

The activity of herbicide and fungicide compositions is enhanced by the incorporation therein of certain alkoxylated fatty amines, amidoamines or imidazolines. The alkoxylation of the amines is conducted with ethylene oxide and either propylene oxide or butylene oxide using a molar ratio of ethylene oxide to the other oxide in the range from 1:14 to 13:2 and to such extent that the molecular weight of the alkoxylated product is kept below 2500.

15 Claims, No Drawings

HERBICIDES AND FUNGICIDES CONTAINING ACTIVITY PROMOTING ADDITIVES

This is a continuation of application Ser. No. 07/384,074 filed Jul. 24, 1989, now abandoned, which in turn is a continuation of Ser. No. 07/078,654, filed Jul. 28, 1987 (abandoned).

The invention relates to additives enhancing the activity of herbicide and fungicide-containing compositions and to the use of these compositions. More particularly, the invention relates to additives which significantly enhance the penetration by herbicides and fungicides of the wax film naturally present on the surface of the plant parts to be treated, more specifically the leaves.

Japanese Patent Application No. 60/051,102 discloses stabilized fungicide compositions which comprise as a fungicide a triazole derivative and a higher alkyl radical and a two polyethoxy or polypropoxy chains-containing amine which is to prevent decomposition of the fungicide during storage of the compositions. In field tests, in which use was made of propoxylated fatty amines in the form of dispersible salts obtained by neutralization with phosphoric acid, the results obtained with these fatty amines were not found satisfactory, which is probably to be attributed to the wholly lypophilic behaviour of these compounds, the hydrophilic properties required for plant leaf penetration (water transport) being insufficiently effective.

Also, from British Patent Specification No. 998,264, for instance, it is known that ethoxylated fatty amines in combination with herbicides, such as Paraquat ® and glyphosate (Round-Up ®) will enhance the absorption of these herbicides through the leaf.

However, an important disadvantage to the ethoxylated fatty amines used up to now in actual practice consists in that upon dissolution in water they form a gel. The problem of gel formation and insufficient dissolution of the wax film may in principle be met by the incorporation into the herbicide composition of nonionic emulsifiers such as a higher alcohol, e.g. isobutanol or polyethylene glycol (PEG), in relatively high concentrations (>20%). But the use of the necessarily high concentrations of these nonionic emulsifiers will be attended with phytotoxic problems, i.e. destruction of underlying cell membranes. Moreover, these ethoxylated fatty amines exclusively have hydrophilic properties, and they lack the lypophilic properties enabling the transport of certain groups of pesticides through the wax film on the plants.

It will be clear that such compounds are not suitable for use in compositions which comprise as active ingredient one or more of the herbicides or fungicides which are at present considered to be the most suitable.

Moreover, it is known that water-emulsified pesticides having lypophilic properties will not or will hardly benefit from the addition of an ethoxylated fatty amine, which as a rule is wholly or practically wholly soluble in water. Also known is an adjuvant used on a practical scale and consisting of tallow amine converted with 1 mole of propylene oxide and 14 moles of ethylene oxide which were randomly mixed in the reaction mixture. Although, as compared with the exclusively ethoxylated tallow amines, this adjuvant displays a lesser tendency to gel formation, i.e. it has a lower water solubility, its properties as far as wax film dissolving capacity and cell membrane penetration are concerned are no better than those of, say, Ethomeen T25 ®.

Therefore, in the field of application of the currently available, most effective, herbicides and fungicides there is still a growing need for additives which on the one hand do not exhibit the above-mentioned detrimental effects and on the other hand significantly improve the effectiveness of the pesticides to be used, more particularly the systemic herbicides and fungicides.

As a result of extensive research and development it has now been found that these desired properties of herbicide and fungicide compositions can be acquired by adding one or more derivatives obtained by reacting fatty amines, fatty amido amines or fatty imidazolines with ethylene oxide and propylene oxide or butylene oxide in separate steps (formation of block polymer) or with random mixtures of ethylene oxide and propylene oxide and/or butylene oxide (copolymer).

It has moreover been found that in order that optimum results may be obtained with the final pesticide compositions
a) the minimum molar ratio between ethylene oxide and propylene oxide or butylene oxide must be 13:2;
b) the maximum molar ratio between ethylene oxide and propylene oxide or butylene oxide must be 1:14;
c) the total molecular weight of the reaction product must be lower than 2500.

The term fatty amines or fatty amido amines/imidazolines as used hereinbefore or hereinafter refers to compounds containing at least one higher 8-22C alkyl radical linked to one or more nitrogen atoms.

The fatty amines or fatty amido amines/imidazolines to be alkoxylated and used in the compositions of this invention are selected from the group consisting of

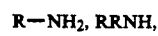

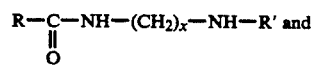

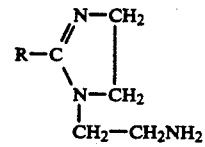

wherein R is an aliphatic hydrocarbon group having 8-22 carbon atoms, R' is hydrogen or an alkyl group having 2-4 carbon atoms and x is an integer from 1 to 6.

According to a special embodiment of the present invention, use is preferably made in the final compositions of compounds of the following structural formulae:

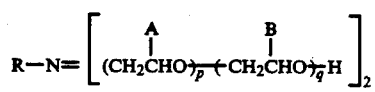   I

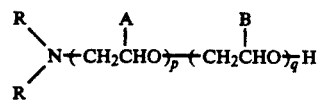   II

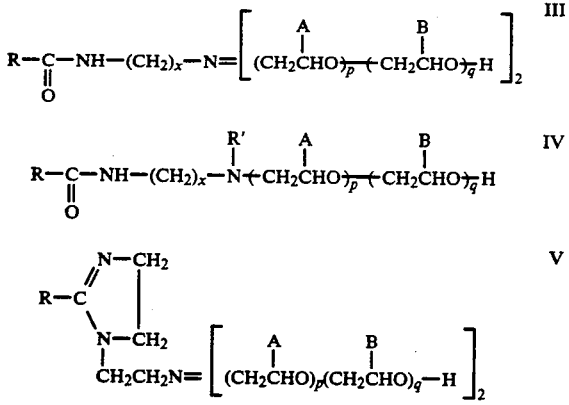

wherein one of A and B is hydrogen and the other is selected from the group consisting of methyl and ethyl, and p and q are integers having a sum of 2-50.

It has been established by experiments that products having a molecular weight higher than 2500 do dissolve the wax film, but do not or hardly penetrate the underlying cell membranes because the molecules are too large.

It has now been found that the additives according to the invention very rapidly dissolve and penetrate the wax film on the plant leaf surface and that after they have passed through the wax film, the underlying cell membranes are penetrated, and the resulting cell leakage will permit the pesticides to enter the cells by this pathway.

It has been found by experiments that the concentration of the additive according to the invention in the solution to be finally applied is of great importance. A too high dosage may give rise to a too fast passage through the outer wax film and the resulting too high concentration underneath the wax film will lead to destruction (strong cell wall lesion and penetration) of the cell membranes, which just leads to blockade of the pesticides. At a proper concentration of the present additives the uptake of the accompanied pesticide is found to be much improved.

For the most optimum combinations of additives and pesticide the additive should be used in a concentration in the range of from 0.01-0.5% by volume and preferably 0.05-0.25% by volume.

Surprisingly, the use of the present additives appears to lead to a correct and optimum balance between hydrophilic and lypophilic properties and they aid the uptake through the leaf of pesticides dissolved in water or emulsified therein. These additives constitute an attractive means of combining maximum dissolution of the wax film, penetration of underlying cell membranes and transport via the hydrophilic and the lypophilic phase, provided that the additives are used in a proper concentration.

It has also been found that the additives according to the invention permit obtaining satisfactory penetration both in monocotyledons and dicotyledons. The additives used up to now, however, which are based on ethoxylated fatty amines, such as Ethomeen ® T25, and rather readily pass through wax films on dicotyledons, will far less readily penetrate silicone wax like surface films on monocotyledons.

The additives according to the invention also offer an essential improvement in connection with the relative humidity at which the pesticide compositions are used.

It has been found that unlike the ethoxylated fatty amines such as Ethomeen ® T25 used up to now the present additives display a satisfactory passage through the plant leaf surface at high (over 65%) and low (20-40%) relative humidity. The ethoxylated fatty amines only showed satisfactory results at high relative humidity.

The additives according to the invention that are to be preferred most are those of the formulae I and II, wherein the molar ratio between ethylene oxide and propylene oxide or butylene oxide is between 50:50 and 20:80. Within these limits the proper lypophilic-hydrophilic balance is found for this type of compounds.

Dispersion of these products in water results in the formation of visible, stable, oily suspensions.

Particularly preferred are additives consisting of ethoxylated and propoxylated tallow amine. Such preferred additives are for instance presented by compounds having the formula

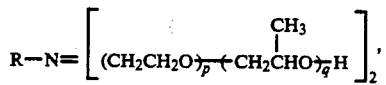

wherein R is the hydrocarbon group of tallow amine, p is 2-3 and q is 4-6, and

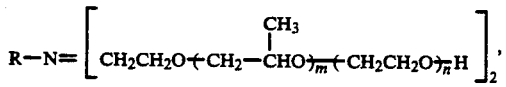

wherein R is the hydrocarbon group of tallow amine, m is 2-3 and n is 2-6.

It will be clear that the invention relates to ready pesticide compositions suitable for practical use which contain one or more of the additives according to the invention in a concentration of 0.01-0.5% by volume and preferably 0.05-0.25% by volume, as well as to concentrated compositions which are mixed and/or diluted in situ for use at the proper concentration. Moreover, the invention relates to the in situ application of the present compositions to plants.

The invention will be further described by the following experiments, which are not to be construed as any limitation on its scope.

The following tables give the results of experiments in which the additives were tested for phytotoxicity and their effects on the activity of the herbicide fluazifop-butyl (Fusilade ®), commercial sterol inhibitors of the firms of X and Y and a sulphonyl urea product.

The phytotoxicity of the additives was measured in two different ways. A first indication is obtained by using a seed germination text.

Garden cress seeds are placed on filter paper in petri dishes. The filter paper is saturated with demineralized water and the additive. The concentrations of the additive are 0.05, 0.5 and 5.0% by volume. The dishes are incubated in the dark for 48 hours at 25° C. Subsequently, the germination percentage and the development of shoot and root are measured.

A second and more realistic approach consists in investigating the effects of the additives after foliar application.

The test species used here are tomato, cabbage, lettuce, garden cress and Johnson grass, which are grown in the greenhouse. The additives are used in concentrations of 0.05, 0.5 and 5.0% by volume. The effects of the additives—growth inhibition and foliage injury—are determined visually.

To determine whether the new additives enhance the activity of fluazifop-butyl the following test is carried out in the greenhouse. Low dosages of Fusilade PP 005 ® (0.12 l/ha) are applied to maize plants with 3 to 4 leaves. Unless stated otherwise the plants in the greenhouse are sprayed with a sprayer fitted with three nozzles (Birchmeier Helico Sapphire 1.2 mm, equipped with a whirling pin 2F-0.6 mm perforated) to provide an application rate of 450 l/ha. Demineralized water is used to prepare the spray liquid. In each experiment every treatment is replicated four times. Upon addition, the concentration of the additive is 0.5% by volume. After two to three weeks the parts of the plant above the ground are harvested. The measured fresh and dry weight are expressed as a percentage of the control's growth. In the Tables I through III below the following test results are summarized:

Table I gives the test results of experiments with fluazifop-butyl (Fusilade ®).
Table II gives the test results of experiments with commercial sterol inhibitors X and Y.
Table III gives the test results of experiments with a sulphonyl urea.

TABLE I

| Adjuvant | EO moles | PO moles | Appr. mol. weight | Soluble in water | Average FW (%) | Average DW (%) |
|---|---|---|---|---|---|---|
| control | — | — | — | — | 100 | 100 |
| fluazifop-butyl | — | — | — | — | 80.7 | 74.7 |
| known chemicals: | | | | | | |
| Ethomeen T25 ® | 15 | 0 | 1000 | gel, dissolved by heating | 19.4 | 42.3 |
| Armoblen T25 ® | 14 | 1 | 1000 | clear solution | 19.4 | 42.3 |
| Propomeen T25 ® | 0 | 15 | 1000 | as salt, slightly cloudy solution | 23.7 | 44.3 |
| preparations of the invention | | | | | | |
| A | 9.5 | 7.5 | 1000 | clear solution | 20.5 | 41.0 |
| B | 5.8 | 11.2 | 1000 | slightly cloudy solution | 21.5 | 42.0 |
| C | 5.0 | 12.0 | 1000 | highly cloudy stable solution | 16.0 | 34.0 | fluazifop-butyl = 0.12 l/ha
adjuvant = 0.5%

TABLE II

Field tests with preparation C for Fuscladium (= scab) in apples. Total number of tests: 21 replicates

| Results of treatment | Foliage injury index derived from % infection acc. to Fisher index |
|---|---|
| a commercial sterol inhibitor of the firm X 1 g of active ingredient + Mancozeb ® 60 g/100 l water + 0.1% prep. C | 4.9 |
| b commercial sterol inhibitor of the firm X 2 g of active ingredient + Mancozeb ® 60 g/100 l water | |
| c commercial sterol inhibitor of the firm Y | 6.4 |
| d control | 78.0 |
| e acceptable for use in actual practice | max. 7.0 |

In the tested concentration the preparation C was neither phytotoxic to fruit nor to trees. The use of the preparation C leads to longer spray intervals and enhanced activity of the fungicide.

TABLE III

Field tests with preparation C as additive compared with mineral oil (Agripon ®, BP oil adjuvant) combined with a sulphonyl urea maize herbicide.

Conditions: 29° C., 35% relative humidity
Crop: maize of Pioneer 496 variety
Application: post-emergence relative to crop
Volume: 200 l water/ha.

| Results of treatment | % weed control (average of 3 replicates) |
|---|---|
| a sulfonyl urea herbicide 15 g of active ingredient/ha + 0.2% C | 65 |
| b sulfonyl urea herbicide 15 g of active ingredient/ha | 40 |
| c sulfonyl urea herbicide 15 g of active ingredient/ha + 0.25% Agripon BP | 50 |
| d sulfonyl urea herbicide 30 g of active ingredient/ha + 0.2% C | 80 |
| e sulfonyl urea herbicide 30 g of active ingredient/ha | 65 |
| f sulfonyl urea herbicide 20 g of active ingredient/ha | 50 |

No crop phytotoxicity. In the first stage of the application, C already displayed a more aggressive effect on the weed than the BP mineral oil, which points to a very high wax film dissolving power of C.

Compound A was prepared from 1960 g of Ethomeen ® T12, the adduct of tallow amine and 2 molecules of ethylene oxide per mole, introduced in a 20 l-autoclave which was flushed with nitrogen for 30 minutes.

The Ethomeen T12 used has an NE-value of 348, an amine content of 1.8%, a colour 1 Gardner and a water content of 0.11%.

Subsequently, 9 ml of KOH 45% 0.3% KOH, based on Ethomeen T12, were added and the mixture was dewatered for two hours at 120° C. (water content: 0.07%). After the mixture had been heated to 180° C., the addition was started of 4210 g of the ethylene/propylene oxide (EO/PO) mixture. As no pressure drop could be observed, the mixture was heated to 195° C. At this temperature the exothermic reaction started. The EO/PO mixture was added over a period of 80 minutes at 185°–195° C. and a pressure of 4.5–6.0 bar. After stirring for 30 minutes at 190° C. the product was cooled to below 60° C. and 2.5 kg of the desired product were isolated (NE-value 1179, Gardner colour 3.4). The compounds B and C were prepared analogously by starting from Ethomeen ® T12 (NE-value 250) and an EO/PO mixture (25% EO and 75% PO) and Ethomeen ® T15 (the adduct of tallow amine and 5 molecules of ethylene oxide per mole and NE-value 845) and 12 moles of PO, respectively. The EO/PO mixture was added over a period of 90 minutes at 180° C. and 5–6 bar and the PO was added over a period of 4 hours at 190°–200° C. and 5–8 bar. The respective end-products were characterized by

| NE (neutralization equivalent) | Gardner colour | Cloud point °C. | Nonionic content (%) |
|---|---|---|---|
| B 1163 | 2–3 | 32 | 2.4 |
| C 1252 | 5 | 19.5 | 5.4 |

I claim:

1. A herbicide composition for foliar application comprising a herbicidally active ingredient and one or more alkoxylated fatty amines as an activity promoting additive, wherein the additive is the reaction product obtained by reacting an amine selected from the group consisting of

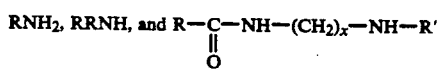

wherein R is an aliphatic hydrocarbon group having 8–22 carbon atoms, R' is hydrogen or an alkyl group having 2–4 carbon atoms and x is an integer from 1 to 6,
with ethyleneoxide and another alkylene oxide selected from the group consisting of propylene oxide and butylene oxide under conditions such that the molar ratio of ethylene oxide to the other alkylene oxide is in the range from 1:14 to 13:2 and the molar weight of the reaction-product is less than 2500.

2. A composition according to claim 1, wherein the additive comprises a compound having a formula selected from the following group

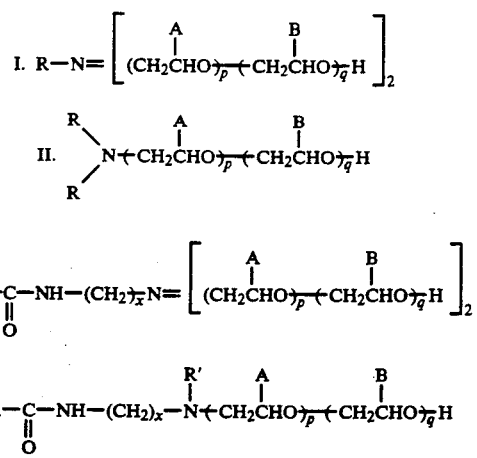

wherein one of A and B is hydrogen and the other is selected from the group consisting of methyl and ethyl, and wherein the ethylene oxide and propylene oxide groups are random or in blocks, and p and q are integers having a sum of 2–50.

3. A composition according to claim 2, wherein the additive comprises a compound having the formula

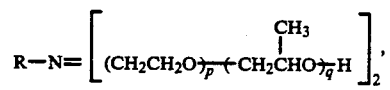

wherein R is the hydrocarbon group of tallow amine, p is 2–3 and q is 4–6.

4. A composition according to claim 1, wherein the additive comprises a compound having the formula

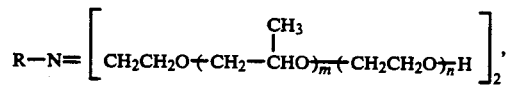

wherein R is the hydrocarbon group of tallow amine, m is 2–3 and n is 2–6.

5. A composition according to claim 2, wherein the additive comprises a compound having the formula

wherein one of A and B is hydrogen and the other is methyl, and wherein the ethylene oxide and propylene oxide groups are random or in blocks.

6. A composition according to claim 5, wherein p:q is between 50:50 and 20:80.

7. A composition according to claim 5, wherein p:q is between 56:44 and 29:71.

8. A composition according to claim 5, wherein p is 5.0 to 9.5 and q is 12.0 to 7.5.

9. A composition according to claim 5, wherein p is 5.0 and q is 12.0.

10. A composition according to claim 5, wherein R is the hydrocarbon group of tallow amine.

11. A composition according to claim 6, wherein R is the hydrocarbon group of tallow amine.

12. A composition according to claim 7, wherein R is the hydrocarbon group of tallow amine.

13. A composition according to claim 8, wherein R is the hydrocarbon group of tallow amine.

14. A composition according to claim 9, wherein R is the hydrocarbon group of tallow amine.

15. A process of treating crops with a herbicide composition comprising treating crops with the composition of claim 1.

* * * * *